(12) United States Patent
Besson

(10) Patent No.: US 8,404,883 B2
(45) Date of Patent: Mar. 26, 2013

(54) PREPARATION OF OXYSULFIDE AND FLUORINATED ORGANIC COMPOUNDS

(75) Inventor: Bernard Besson, Les Echets (FR)

(73) Assignee: Rhodia Operations, Aubervilliers (FR)

( * ) Notice: Subject to any disclaimer, the term of this patent is extended or adjusted under 35 U.S.C. 154(b) by 905 days.

(21) Appl. No.: 12/298,354

(22) PCT Filed: Apr. 18, 2007

(86) PCT No.: PCT/FR2007/000649
§ 371 (c)(1),
(2), (4) Date: Mar. 30, 2009

(87) PCT Pub. No.: WO2007/128893
PCT Pub. Date: Nov. 15, 2007

(65) Prior Publication Data
US 2009/0216036 A1    Aug. 27, 2009

(30) Foreign Application Priority Data
Apr. 26, 2006  (FR) ...................................... 06 03715

(51) Int. Cl.
*C07C 313/04* (2006.01)

(52) U.S. Cl. ......................................................... 558/61
(58) Field of Classification Search .................... 558/61
See application file for complete search history.

(56) References Cited

U.S. PATENT DOCUMENTS
6,464,895 B2 * 10/2002 Forat et al. ............... 252/182.12

FOREIGN PATENT DOCUMENTS
EP    0165135 A1 *  5/1985
EP    0 735 023       10/1996

* cited by examiner

*Primary Examiner* — Joseph Kosack
(74) *Attorney, Agent, or Firm* — SNR Denton US LLP

(57) ABSTRACT

Oxysulfide and fluorinated organic compounds, for example, perfluoroalkanesulfinic and sulfonic acids, and preferably trifluoromethanesulfinic and trifluoromethanesulfonic acids in salt form, are prepared by reacting, in the presence of an aprotic polar organic solvent: (i) a fluorocarboxylic acid having the formula Ea-CF$_2$—COOH (I), wherein Ea is an atom or an electroattracting group at least partially forming a salt with an organic or inorganic cation; with (ii) a sulfur oxide, preferably sulfur dioxide, and further wherein the ratio of the number of moles of sulfur oxide to the number of moles of fluorocarboxylic acid is less than 1, preferably less than 0.99.

26 Claims, No Drawings

PREPARATION OF OXYSULFIDE AND FLUORINATED ORGANIC COMPOUNDS

CROSS-REFERENCE TO PRIORITY/PCT APPLICATIONS

This application is a national phase of PCT/FR 2007/000649, filed Apr. 18, 2007 and designating the United States (published in the French language on Nov. 15, 2007, as WO 2007/128893 A1; the title and abstract were also published in English), which claims priority under 35 U.S.C. §119 of FR 0603715, filed Apr. 26, 2006, each hereby expressly incorporated by reference in its entirety and each assigned to the assignee hereof.

A subject matter of the present invention is an improved process for the preparation of oxysulfide and fluorinated organic derivatives.

More specifically, the invention relates to the preparation of fluoroalkanesulfinic and -sulfonic acids and their salts.

The invention is targeted at the preparation of perfluoroalkanesulfinic and -sulfonic acids and preferably trifluoromethanesulfinic acid and trifluoromethanesulfonic acid in the salified form.

Perhaloalkanesulfonic acids and more particularly trifluoromethanesulfonic acid are used as catalysts or as intermediates in organic synthesis.

A description has been given, in EP 0 735 023, of the synthesis of oxysulfide and fluorinated organic derivatives, in particular of perfluoromethanesulfinic acid in the salified form, by reaction in a polar organic solvent of a fluorocarboxylic acid of formula Ea-CF$_2$—COOH, where EA represents an electron-withdrawing atom or group, at least partially salified by an organic or inorganic cation, and of a sulfur oxide, in particular sulfur dioxide, and heating the resulting mixture at a temperature of between 100° C. and 200° C. for a time of between 30 min and 20 hours.

The relative amounts of said starting fluorocarboxylic acid and of sulfur oxide, preferably dioxide, are such that the ratio of the number of sulfur atoms per mole of fluorocarboxylic acid is between 1 and 10, advantageously in the vicinity of 2.

According to EP 0 735 023, two conditions appear to be essential, namely the choice of the solvent and the content of protons which can be released into the reaction mixture.

The yields of oxysulfide and fluorinated organic derivatives obtained range between 30 and 55% with a reaction selectivity of the order of 50%, with the exception of example 6, where a selectivity of 85% is obtained by virtue of the use of very rigorous anhydrous conditions, which is highly restricting from an industrial viewpoint.

Furthermore, it should be noted that, in order to prevent excessively great decomposition of the final product and thus to provide good selectivity of the reaction, it is preferable not to attempt to completely convert the starting fluorocarboxylic acid. Thus, the reaction is carried out until a degree of conversion of 40 to 80%, preferably of 50 to 70%, is obtained.

On continuing its research, the Applicant Company has found that this process can be improved if the sulfination reaction is carried out while limiting the amount of sulfur oxide introduced.

More specifically, the subject matter of the present invention is a process for the preparation of an oxysulfide and fluorinated organic derivative comprising the reaction, in the presence of a polar aprotic organic solvent:

(i) of a fluorocarboxylic acid of formula

Ea-CF$_2$—COOH  (I), where Ea represents an electron-withdrawing atom or group, at least partly salified by an organic or inorganic cation, (ii) and of a sulfur oxide, preferably sulfur dioxide, said process being characterized in that the ratio of the number of moles of sulfur oxide to the number of moles of fluorocarboxylic acid is less than 1, preferably less than 0.99.

In accordance with the process of the invention, it has been found that the selectivity of the sulfination reaction can be improved provided that the amount of sulfur oxide, preferably sulfur dioxide, is less than the stoichiometric amount. Thus, the ratio defined above is chosen to be less than 1, preferably less than 0.99 and more preferably between 0.4 and 0.95.

Generally, in such reactions, the amounts of sulfur oxide are in large stoichiometric excesses and it was not at all obvious to a person skilled in the art that the reduction in said ratio would make it possible to obtain the advantages introduced by the invention.

Not only is the selectivity of the reaction improved but the process is also carried out more easily owing to the fact that the pressure of the reaction can be lowered and can become equal to atmospheric pressure.

In accordance with the process of the invention, a fluorocarboxylic acid in the salified form is reacted with a sulfur oxide.

In the fluorocarboxylic acid corresponding to the formula (I), the entity Ea, which exerts an electron-withdrawing effect on the difluorinated carbon atom, is preferably chosen from the functional groups having a Hammett constant $\sigma_p$ at least equal to 0.1.

In addition, it is preferable for the inductive component of $\sigma_p$, $\sigma_I$, to be at least equal to 0.2, advantageously to 0.3.

In this respect, reference will be made to the work by Jerry March, Advanced Organic Chemistry, 4th edition, John Wiley and Sons, 1992, chapter 9, pp. 278-286, and in particular to table 9.4 of this section.

More particularly, the electron-withdrawing entity Ea is a fluorine atom.

The corresponding fluorocarboxylic acid is a halofluoroacetic acid of formula (Ia):

X—CF$_2$—COOH  (Ia)

in said formula:
X is a fluorine atom.
Ea can also advantageously be chosen from carbonyl, sulfone and perfluoroalkyl groups.

Fluorocarboxylic acids of this type which can be used correspond to the formula (Ib)

R-G-CF$_2$—COOH  (Ib)

in said formula:
G represents a C=O or S=O functional group,
G represents a perfluoroalkylene —(CF$_2$)$_n$ group where n is greater than or equal 1,
R represents a halogen atom, preferably a chlorine or fluorine atom,
R represents any inorganic or organic residue, preferably an organic radical, such as aryl, alkyl or aralkyl, which is optionally substituted,
R can also represent a solid inorganic or organic support, such as a resin.

The preferred meanings of the organic radicals are given below.

The term "alkyl" is understood to mean a linear or branched C$_1$-C$_{15}$, preferably C$_1$-C$_{10}$ and more preferably still $C_1$-$C_4$ hydrocarbon chain. Examples of preferred alkyl groups are in particular methyl, ethyl, propyl, isopropyl, butyl, isobutyl or t-butyl.

The term "cycloalkyl" is understood to mean a cyclic hydrocarbon group which is a $C_3$-$C_8$ monocyclic group, preferably a cyclopentyl or cyclohexyl group, or a $C_4$-$C_{18}$ polycyclic (bi or tricyclic) group, in particular adamantyl or norbornyl.

The term "aryl" is understood to mean a mono- or polycyclic aromatic group, preferably a $C_6$-$C_{20}$ mono- or bicyclic aromatic group, preferably phenyl or naphthyl. When the group is polycyclic, that is to say that it comprises more than one cyclic nucleus, the cyclic nuclei can be fused in pairs or attached in pairs via a bonds. Examples of ($C_6$-$C_{18}$)aryl groups are in particular phenyl or naphthyl.

The term "arylalkyl" is understood to mean a linear or branched hydrocarbon group carrying a $C_7$-$C_{12}$ monocyclic aromatic ring, preferably benzyl, the aliphatic chain comprising 1 or 2 carbon atoms.

It should be noted that, as soon as one of the groups comprises a ring, the latter can be substituted by one or more, preferably two, substituents. The substituent can be of any nature, provided that it does interfere with the reaction. Mention may in particular be made, as preferred examples, of alkyl or alkoxy groups having from 1 to 4 carbon atoms.

In the context of the invention, alkyl groups are the preferred organic radicals.

In the case where G represents a perfluoroalkylene group —$(CF_2)_n$—, n is advantageously between 1 and 10, preferably between 1 and 5. Still in this case, R can also represent a halogen atom, in particular fluorine.

Generally, except in the case where the fluorocarboxylic acid is a polymer, the total number of carbon atoms of the fluorocarboxylic acid advantageously does not exceed 30. It is preferably between 2 and 12.

The counterions capable of forming a salt with said fluorocarboxylic acid are advantageously bulky. Thus, preference is given to alkali metal salts, advantageously when said metal is chosen from sodium potassium, rubidium and cesium.

Preferably, the metal is from a period with a rank greater than that of sodium, in particular potassium or cesium.

It is also possible to improve the reaction by using cations which are either naturally bulky, such as quaternary ammonium or quaternary phosphonium cations, or which are rendered bulky by the addition of chelating agents or, preferably, cryptands, such as, for example, crown ethers or derivatives which comprise both amine groups and oxygen atoms.

Use is preferably made, as quaternary ammonium or phosphonium cations, of tetraalkylammonium or -phosphonium, trialkylbenzylammonium or -phosphonium or tetraarylammonium or -phosphonium, the identical or different alkyl groups of which represent a linear or branched alkyl chain having from 4 to 12 carbon atoms, preferably from 4 to 6 carbon atoms, and the aryl group of which is advantageously a phenyl group.

The tetrabutylammonium cation is preferably chosen.

Salts of perfluorocarboxylic acids can advantageously be used, such as alkali metal, in particular potassium, trifluoroacetate, perfluoropropionate, perfluorobutyrate or perfluorooctanoate.

The invention preferably relates to the preparation of trifluoromethanesulfinic acid in a salified form, preferably in the form of an alkali metal salt and more preferably the potassium salt.

The sulfur oxide, preferably sulfur dioxide, can be employed in the gaseous form. It can also be introduced in the form of a solution, in the organic solvent chosen for the reaction, at a concentration generally varying between 1 and 10% by weight, preferably between 3 and 6% by weight.

According to the characteristic of the process of the invention, the ratio of the number of moles of sulfur oxide to the number of moles of fluorocarboxylic acid is less than 1, preferably less than 0.99.

Said ratio is preferably chosen between 0.4 and 0.95 and preferentially between 0.7 and 0.9.

The process of the invention consists in carrying out the sulfination reaction in an organic solvent.

The latter plays an important role in the present invention and must be aprotic and advantageously polar and comprise very few impurities carrying acid hydrogen.

The term "aprotic solvent" is understood to mean a solvent which, in the Lewis theory, does not have protons to release.

Recourse is had to a solvent which is sufficiently stable under the reaction conditions.

It is desirable for the solvent to dissolve the fluorocarboxylic acid salt, either at least partially or preferably completely.

Thus, the organic solvent is chosen to be polar. It is thus preferable for the polar aprotic solvent which can be used to have a significant dipole moment. Thus, its relative dielectric constant $\in$ is advantageously at least equal to approximately 5. Preferably, its dielectric constant is less than or equal to 50 and greater than or equal to 5 and is in particular between 30 and 40.

In order to determine if the organic solvent meets the dielectric constant conditions set out above, reference may be made, inter alia, to the tables of the work: Techniques of Chemistry; II—Organic solvents—p. 536 et seq., 3rd edition (1970).

In addition, it is preferable for the solvents of the invention to be capable of thoroughly solvating the cations, which means that the solvent exhibits certain properties of basicity within the Lewis meaning.

In order to determine if a solvent satisfies this requirement, its basicity is assessed with reference to the "donor number". A polar organic solvent exhibiting a donor number of greater than 10, preferably of greater than or equal to 20, is chosen. The upper limit does not exhibit any critical nature. The choice is preferably made of an organic solvent having a donor number of between 10 and 30.

It will be remembered that the "donor number", denoted in abbreviated fashion by DN, gives an indication with regard to the nucleophilic nature of the solvent and reveals its ability to donate its doublet.

The work by Christian Reichardt, [Solvents and Solvent Effects in Organic Chemistry, VCH, p. 19 (1990)], includes the definition of the "donor number", which is defined as the negative ($-\Delta H$) of the enthalpy (kcal/mol) of the interaction between the solvent and antimony pentachloride in a dilute dichloroethane solution.

According to the present invention, the polar solvent or solvents do not exhibit acid hydrogen; in particular when the polar nature of the solvent or solvents is obtained by the presence of electron-withdrawing groups, it is desirable for hydrogen not to be present on the atom in the α position with respect to the electron-withdrawing functional group.

More generally, it is preferable for the pKa corresponding to the first acidity of the solvent to be at least equal to approximately 20 ("approximately" emphasizing that only the first FIGURE is significant), advantageously at least equal to approximately 25, preferably between 25 and 35.

The acid nature can also be expressed by the acceptor number AN of the solvent, as defined by Christian Reichardt [Solvents and Solvent Effects in Organic Chemistry, 2nd edition, VCH (RFA), 1990, pages 23-24].

Advantageously, this acceptor number AN is less than 20, in particular less than 18.

The solvents which meet the various requirements and which give good results can in particular be solvents of amide type. The amides also include the amides having a specific nature, such as tetrasubstituted ureas and monosubstituted lactams. The amides are preferably substituted (disubstituted for ordinary amides). Mention may be made, for example, of amides, such as N,N-dimethylformamide (DMF), N,N-diethylformamide or N,N-dimethylacetamide; or pyrrolidone derivatives, such as N-methylpyrrolidone.

Another particularly advantageous category of solvent is composed of ethers, whether symmetric or asymmetric and whether open or closed. The various derivatives of glycol ethers, such as the various glymes, for example diglyme, have to be included in the category of the ethers.

Use is preferably made, among the abovementioned solvents, of DMF.

The amount of organic solvent to be employed is determined as a function of the nature of the organic solvent chosen.

It is determined so that the concentration of the fluorocarboxylic acid in the organic solvent is preferably between 1 and 30% by weight and more preferably between 10 and 20% by weight.

According to the preferred conditions for implementing the process of the invention, it is desired to control the content of impurities present in the reaction medium.

The content of labile hydrogen atoms of the system or more precisely of releasable protons carried by its various components, including their impurities, must be lower than the content of fluorine-comprising groups released by the decomposition of the fluorocarboxylic acids.

The term "labile hydrogen atom" or "releasable proton" is understood to mean a hydrogen atom which is capable of being pulled off in the form of a proton by a strong base. In practice, they are the protons of the acid functional groups which exhibit a pKa of less than approximately 20.

The lower the content of releasable protons, the less the risk of side reactions and the better the yield.

The content of releasable protons present in the medium is at most equal to 20% of the starting molar concentration of said fluorocarboxylic acid.

Advantageously, this content is at most equal to 10%, preferably to 1% (in moles), with respect to the starting content of said fluorocarboxylic acid.

The main molecule carrying labile hydrogen atoms is generally water, which is capable of releasing up to two protons per molecule.

Generally, it is preferable to use dehydrated reactants and solvents, so that the content by weight of water in the reactant is at most equal to 1 per 1000, with respect to the total weight of the reactant.

Depending on the combined reaction conditions, such water contents may be satisfactory but, in some cases, it may be advantageous to operate at lower levels, for example in the order of 1 per 10 000.

However, it is not necessarily essential to remove all the water and a water/fluorocarboxylic acid molar ratio of less than 10% can be tolerated.

As mentioned in EP 0 735 023, it is desirable for the metal impurities to be in low amounts. Metal elements may present as impurities introduced in particular by the reactants or the solvent or else by the metal equipment as a result of corrosion.

Thus, in order not to introduce additional contamination by metals, it is important for the starting fluorocarboxylic acid salt employed to be prepared by reaction of a base with the fluorocarboxylic acid of formula (I) under conditions such that the base is introduced in an amount in the region of and preferably equal to the stoichiometric amount.

More generally, it may be indicated that the two categories of metals, namely the transition elements comprising two valence states (such as copper) and the elements from group VIII (in particular platinum ore metals, which is the group composed of platinum, osmium, iridium, palladium, rhodium and ruthenium), have to be present in the medium at a content, expressed with respect to the fluorocarboxylic acid, at most equal to 1000 molar ppm, preferably to 10 molar ppm.

In the present description, reference is made to the Supplement to the Bulletin de la Société Chimique de France, No. 1, January 1966, where a Periodic Table of the Elements was published.

In accordance with the process of the invention, the fluorocarboxylic acid in the salified form, the sulfur oxide and the organic solvent are brought into contact.

The processing can be carried out batchwise or continuously.

The methods of introduction are not critical but some are preferred.

According to a batchwise employment, the salt of the fluorocarboxylic acid can be introduced into the organic solvent and then the sulfur oxide can be added, in all or in fractions; the sulfur oxide can be introduced in the gaseous form by absorption in the abovementioned medium or else can also be introduced in solution in an organic solvent, preferably that of the reaction.

The reaction is carried out in a conventional reactor equipped with a heating device (heat exchanger) and with a stirring device, for example stirring using a propeller.

The reaction mixture is subsequently heated.

According to a continuous embodiment, recourse is had to a device which makes possible continuous processing, such as several reactors in cascade or a tube equipped with a jacket in which a heat-exchange fluid circulates, the characteristics of the heat-exchange fluid making it possible to achieve the desired reaction temperature.

In this case, the device is fed with the salt of the fluorocarboxylic acid as a mixture with the organic solvent, and sulfur dioxide is introduced.

The latter can be added in the feed solution comprising the fluorocarboxylic acid and the organic solvent or else it can be introduced at various points of the device; it being possible for delivery to take place in the head space of the reactor or in the reaction mass.

Subsequently, heating is carried out until the desired degree of conversion is obtained.

In accordance with the process of the invention, the heating of the reaction mixture advantageously takes place at a temperature of between 100° C. and 200° C., preferably between 120° C. and 160° C.

The sulfination reaction is advantageously carried out at atmospheric pressure but higher pressures may also be used. Thus, a total absolute pressure chosen between 1 and 20 bar and preferably between 1 and 3 bar may be suitable.

The duration of a heating can vary widely as a function of the reaction temperature chosen. It can vary between approximately 30 min and at most one day. It is advantageously from more than one hour to less than 20 hours and more preferably between 2 hours and 7 hours.

According to the continuous embodiment, the mean residence time, which is defined as the ratio of the volume of the reaction mass to the feed flow rate, is between 30 min and 10 hours and more preferably between 2 hours and 4 hours.

When said sulfur oxide is sulfur dioxide, the mixture resulting from the sulfination stage can comprise two phases: a liquid phase, where a portion at least of said acid and of the sulfur dioxide are dissolved in said solvent, and a gas phase essentially comprising sulfur dioxide and carbon dioxide gas formed during the reaction.

In order to avoid excessively great decomposition of the final product and thus to provide good selectivity of the reaction, it is preferable not to attempt to completely convert the starting fluorocarboxylic acid.

The progress of the reaction can be monitored by the degree of conversion (DC) of the acid, which is the molar ratio of the amount of acid disappeared to the initial amount of acid in the reaction medium, this degree being easily calculated after quantitatively determining the acid remaining in the medium.

Advantageously, the reaction will be carried out only up to the achievement of a degree of conversion of 30 to 80%, preferably of 40 to 60%, and then the reaction products will be separated. It is possible to thus achieve a selectivity of greater than 80%, and yet even of greater than 90%, expressed by the desired product/fluorocarboxylic acid converted molar ratio.

Once the desired degree of conversion has been achieved, the reaction mixture can be treated in a way known per se in order to separate the product obtained, it being possible for the starting materials to be recycled in order to produce an additional amount of the targeted organic derivative.

When said sulfur oxide is sulfur dioxide, the product obtained by heating the reaction medium is a sulfinic acid salt, the counterion of which is that of the starting fluorocarboxylic acid salt.

In order to separate the reaction product, an advantageous possibility consists in carrying out an additional conversion to give a relatively volatile and easily distillable derivative.

Thus, for example, during the reaction between $SO_2$ and the salts of trifluoroacetic acid $CF_3CO_2H$, the salts of trifluoromethylsulfinic acid $CF_3SO_2H$ obtained can easily be converted in the presence of chlorine $Cl_2$ to give $CF_3SO_2Cl$ (this reaction is general to the acids used and in particular to perfluoroalkanesulfinic acids $R_fSO_2H$). This reaction advantageously makes it possible to separate $CF_3SO_2Cl$ by distillation while leaving inorganic chlorides and the salt of trifluoromethanesulfonic acid intact in the reaction medium, which can thus be reused to continue the reaction with the sulfur oxide. This reaction is common to the various fluorinated sulfinic acids which can be obtained according to the invention. This example can be generalized to the separation of all types of oxysulfide and fluorinated organic derivatives obtained according to the invention which are capable of being converted by an appropriate reaction to give more volatile products.

In order to change from the sulfinic acid to the corresponding sulfonic acid, it is appropriate to subject the reaction product or the purified reaction product to an oxidation, known in itself, in particular by means of aqueous hydrogen peroxide solution or sodium hypochlorite. A process for the purification of sodium trifluoromethylsulfinate and for the oxidation to give the sulfonate which can be applied according to the invention is described in the European patent application published under the number EP-A-0 396 458.

The sulfinic or sulfonic acid salts thus obtained can be converted to the corresponding free acids in an acid medium. Sulfuric acid, optionally in the oleum form, or else hydrochloric acid is preferably used.

The reaction products, salts or free acids, can be easily isolated and can be employed in subsequent stages of organic synthesis. Thus, for example, the sulfinyl chlorides obtained from fluorinated sulfinic acids prepared according to the invention can be put to use.

The examples which follow illustrate the invention without, however, limiting it.

The meanings of the abbreviations used in the examples are given below.

The degree of conversion (DC) corresponds to the ratio of the number of moles of substrate converted to the number of moles of substrate charged.

The yield (RY) corresponds to the ratio of the number of moles of product formed to the number of moles of substrate charged.

The selectivity (CY) corresponds to the ratio of the number of moles of product formed to the number of moles of substrate converted during the reaction.

KTFA means "potassium trifluoroacetate".

Examples 1 and 2 given below describe a batchwise method of preparation.

Examples 3 to 6 illustrate a continuous embodiment.

EXAMPLE 1

Preparation of Potassium Trifluoromethylsulfinate 125.5 g of dimethylformamide are charged at ambient temperature (approximately 20° C.) to a 500 cm³ reactor equipped with a jacket, a central mechanical stirrer and an outlet to the atmosphere and an acetone/dry ice condenser which makes possible the reflux of sulfur dioxide.

25.5 g of potassium trifluoroacetate are introduced into the DMF.

6.9 g of sulfur dioxide are subsequently charged via a capillary connected to a bottle of sulfur dioxide under pressure.

The mixture is heated at 140° C. and at atmospheric pressure.

The molar ratio of $SO_2$ to the KTFA is 0.64.

After 4 hours 25 min. analysis by ion chromatography gives the following results:

| | |
|---|---|
| Degree of conversion of the potassium trifluoroacetate: | 57.1% |
| Yield of potassium trifluoromethylsulfinate: | 52.8% |
| Selectivity for potassium trifluoromethylsulfinate: | 92.4% |

A very good reaction selectivity is recorded.

EXAMPLE 2

Preparation of Potassium Trifluoromethylsulfinate

Example 1 is repeated, except for the difference that the molar ratio of $SO_2$ with respect to the KTFA is 0.72.

116.2 g of dimethylformamide are charged to an installation as described in example 1, 23.8 g of potassium trifluoroacetate are charged to the DMF and 7.2 g of sulfur dioxide are added with bubbling.

The mixture is heated at 137° C. and at atmospheric pressure.

After 5 hours, analysis by ion chromatography gives the following results:

| | |
|---|---|
| Degree of conversion of the potassium trifluoroacetate: | 52% |
| Yield of potassium trifluoromethylsulfinate: | 47.4% |
| Selectivity for potassium trifluoromethylsulfinate: | 90.4% |

A very good reaction selectivity is recorded.

EXAMPLES 3 to 6

Preparation of Potassium Trifluoromethylsulfinate

A series of examples according to a continuous route is given below.

In the various examples which follow, use is made of a reactor of cylindrical shape which is heated by a heat-exchange fluid (silicone oil) circulating in a jacket.

The reactor is composed of four compartments which are in communication via orifices situated at the foot of the walls separating them.

Thus, the reaction liquid which is fed into the first compartment from a tank and via a metering pump can pass into the second compartment and so on as far as the final compartment.

The reaction mass exits by overflowing the final compartment and is collected in a receptacle via gravity.

Each compartment is equipped with a mechanical stirring system comprising a vertical shaft, with an independent atmospheric pressure breathing system and with a temperature probe, and also with a side opening which makes it possible to withdraw the liquid phase via a syringe.

The working volume, that is to say the volume of reaction mass of each compartment, is approximately 50 cm$^3$.

EXAMPLE 3

The reactor is fed at a flow rate of 1.3 cm$^3 \cdot$min$^{-1}$ with a solution having the following composition:

| | |
|---|---|
| Dimethylformamide: | 82.1% |
| Potassium trifluoroacetate: | 13.4% |
| Sulfur dioxide: | 4.5% |

The molar ratio of SO$_2$ with respect to the KTFA is 0.8.

The four compartments are heated at 140° C.

After an operating time of 21 hours, the stationary state is achieved.

The composition of the various compartments are analyzed by ion chromatography.

It is found that, in each compartment, the conversion of the KTFA, the yield of trifluoromethylsulfinate and the selectivity for trifluoromethylsulfinate are as follows:

TABLE I

| Compartment No. | KTFA conversion | Yield of trifluoromethylsulfinate | Selectivity for trifluoromethylsulfinate |
|---|---|---|---|
| 1 | 11.7% | 11.3% | 97.3% |
| 2 | 24.4% | 23.6% | 96.8% |
| 3 | 31.5% | 31.3% | 99.5% |
| 4 | 37.0% | 36.3% | 98.2% |

EXAMPLE 4

The reactor is fed, at a flow rate of 0.7 cm$^3 \cdot$min$^{-1}$, with a solution having the following composition:

| | |
|---|---|
| Dimethylformamide: | 82.1% |
| Potassium trifluoroacetate: | 13.4% |
| Sulfur dioxide | 4.5% |

The molar ratio of SO$_2$ with respect to the KTFA is 0.8.

The four compartments are heated at 135° C.

After an operating time of 5 hours, it can be considered that the stationary state is achieved.

The compositions of the various compartments are analyzed by ion chromatography.

It is found that, in each compartment, the conversion of the KTFA, the yield of trifluoromethylsulfinate and the selectivity for trifluoromethylsulfinate are as follows:

TABLE II

| Compartment No. | KTFA conversion | Yield of trifluoromethylsulfinate | Selectivity for trifluoromethylsulfinate |
|---|---|---|---|
| 1 | 21.2% | 21.1% | 99.1% |
| 2 | 33.5% | 32.2% | 95.9% |
| 3 | 38.0% | 36.8% | 97.1% |
| 4 | 40.8% | 38.0% | 93.2% |

EXAMPLE 5

The reactor is fed, at a flow rate of 1.7 cm$^3 \cdot$min$^{-1}$, with a solution having the following composition:

| | |
|---|---|
| Dimethylformamide: | 78.5% |
| Potassium trifluoroacetate: | 16.1% |
| Sulfur dioxide: | 5.4% |

The molar ratio of SO$_2$ with respect to the KTFA is 0.8.

The four compartments are heated at 140° C.

After an operating time of 5 hours, it may be considered that the stationary state is achieved.

The compositions of the various compartments are analyzed by ion chromatography.

It is found that, in the fourth compartment, the conversion of the KTFA and the yield of trifluoromethylsulfinate are 29.1% and 28.1% respectively.

The selectivity for potassium trifluoromethylsulfinate is 96.4%.

EXAMPLE 6

The reactor is fed, at a flow rate of 1.7 cm³·min⁻¹, with a solution having the following composition:

| | |
|---|---|
| Dimethylformamide: | 83.1% |
| Potassium trifluoroacetate: | 13.5% |
| Sulfur dioxide: | 3.4% |

The molar ratio of $SO_2$ with respect to the KTFA is 0.6.
The four compartments are heated at 135° C.
After an operating time of 5 hours, it may be considered that the stationary state is achieved.
The compositions of the various compartments are analyzed by ion chromatography.
It is found that, in the fourth compartment, the conversion of the KTFA and the yield of trifluoromethylsulfinate are 37% and 35% respectively.
The selectivity for potassium trifluoromethylsulfinate is 94%.

What is claimed is:

1. A process for the preparation of an oxysulfide and fluorinated organic compound, comprising reacting, in the presence of a polar aprotic organic solvent:
   (i) a fluorocarboxylic acid having the formula Ea-$CF_2$—COOH (I), wherein Ea is an electron-withdrawing atom or group, at least partly salified by an organic or inorganic cation, with
   (ii) a sulfur oxide, and further wherein the ratio of the number of moles of sulfur oxide to the number of moles of fluorocarboxylic acid is less than 1.

2. The process as defined by claim 1, wherein the ratio of the number of moles of sulfur oxide to the number of moles of fluorocarboxylic acid ranges from 0.4 to 0.95.

3. The process as defined by claim 1, wherein the fluorocarboxylic acid having the formula (I), Ea, which exerts an electron-withdrawing effect on the difluorinated carbon atom, is a functional group having a Hammett constant $\sigma_p$ at least equal to 0.1.

4. The process as defined by claim 1, wherein said fluorocarboxylic acid is a halofluoroacetic acid having formula (Ia):

X—$CF_2$—COOH     (Ia)

wherein X is a halogen atom.

5. The process as defined by claim 1, wherein said fluorocarboxylic acid is an acid having formula (Ib):

R-G-$CF_2$—COOH     (Ib)

wherein:
   G is a C=O or S=O functional group, or a perfluoroalkylene —$(CF_2)_n$ group wherein n is greater than or equal to 1, and
   R is a halogen atom, or an organic radical selected from the group consisting of aryl, alkyl and aralkyl radicals, which are optionally substituted, or a solid inorganic or organic support.

6. The process defined by claim 5, wherein said fluorocarboxylic acid is a halofluoroacetic acid having formula (Ib), in which G is a perfluoroalkylene group —$(CF_2)_n$—, with n ranging from 1 to 10.

7. The process as defined by claim 4, wherein said fluorocarboxylic acid is trifluoroacetic acid.

8. The process as defined by claim 1, wherein said acid is salified with an alkali metal cation selected from among sodium, potassium, rubidium and cesium or with a quaternary ammonium or phosphonium.

9. The process as defined by claim 8, wherein said acid is in the potassium salt form.

10. The process as defined by claim 1, wherein said sulfur oxide comprises sulfur dioxide in the gaseous form or in solution, in said organic solvent, at a concentration ranging from 1 to 10% by weight.

11. The process as defined by claim 1, wherein said organic solvent comprises an aprotic solvent having a dielectric constant of less than or equal to 50 and greater than or equal to 5.

12. The process as defined by claim 11, wherein said polar organic solvent exhibits a donor number of greater than 10.

13. The process as defined by claim 1, wherein said organic solvent exhibits an acceptor number of less than 20.

14. The process as defined by claim 1, wherein said organic solvent exhibits a pKa corresponding to its first acidity which is at least equal to 20.

15. The process as defined by claim 1, wherein said organic solvent is selected from among N-disubstituted amides, tetrasubstituted ureas, monosubstituted lactams, and cyclic ethers.

16. The process as defined by claim 1, wherein said organic solvent comprises N,N-dimethylformamide (DMF), N,N-diethylformamide or N,N-dimethylacetamide.

17. The process as defined by claim 1, wherein the content of releasable protons of the reaction medium is at most equal to 20% of the molar concentration of said fluorocarboxylic acid.

18. The process as defined by claim 1, wherein the water content of the reaction medium is less than 10% of the molar concentration of said fluorocarboxylic acid.

19. The process as defined by claim 1, wherein the content of the transition elements comprising two valence states and of the elements from Group VIII is less than 1,000 molar ppm, with respect to said fluorocarboxylic acid.

20. The process as defined by claim 1, carried out continuously or batchwise.

21. The process as defined by claim 1, wherein the fluorocarboxylic acid in the salified form, the sulfur oxide and the organic solvent are contacted and the reaction mixture is heated at a temperature ranging from 100° C. to 200° C.

22. The process as defined by claim 1, comprising a sulfination reaction carried out at atmospheric pressure.

23. The process as defined by claim 1, wherein the resulting reaction mixture comprises two phases: a liquid phase, wherein a portion at least of said acid and of the sulfur dioxide are dissolved in said solvent, and a gas phase comprising sulfur dioxide and carbon dioxide gas formed during the reaction.

24. The process as defined by claim 1, comprising separating the reaction products when the degree of conversion of said fluorocarboxylic acid ranges from 30 to 80%.

25. The process as defined by claim 1, wherein at a subsequent stage, the salt of sulfinic acid obtained is oxidized by contacting the latter with an oxidizing reagent.

26. The process as defined by claim 1, wherein said sulfur oxide comprises sulfur dioxide and said ratio is less than 0.99.

* * * * *